US012558469B2

(12) United States Patent　　　　　(10) Patent No.: US 12,558,469 B2
Carlson et al.　　　　　　　　　　　　　(45) Date of Patent: Feb. 24, 2026

(54) SYSTEMS AND METHODS FOR CONVERTING AN APHERESIS FLUID PROCESSING CIRCUIT TO SINGLE OR DOUBLE NEEDLE MODE

(71) Applicant: Fenwal, Inc., Lake Zurich, IL (US)

(72) Inventors: Angela N. Carlson, Arlington Heights, IL (US); Gregory Coultas, Chicago, IL (US); Lan T. Nguyen, Vernon Hills, IL (US); Kevin Schalte, Crystal Lake, IL (US); Grover Burkett, Gilberts, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 17/880,357

(22) Filed: Aug. 3, 2022

(65) Prior Publication Data

US 2023/0043534 A1　　Feb. 9, 2023

Related U.S. Application Data

(60) Provisional application No. 63/230,473, filed on Aug. 6, 2021.

(51) Int. Cl.
　　*A61M 1/34*　　　　　(2006.01)
　　*A61M 1/36*　　　　　(2006.01)
　　*A61M 25/00*　　　　(2006.01)
(52) U.S. Cl.
　　CPC ........ *A61M 1/3401* (2022.05); *A61M 1/3403* (2014.02); *A61M 1/3496* (2013.01); *A61M 1/3659* (2014.02); *A61M 2025/0031* (2013.01)
(58) Field of Classification Search
　　CPC .............. A61M 1/3401; A61M 1/3403; A61M 1/3496; A61M 1/3659; A61M 2025/0031; A61M 1/304; A61M 1/305; A61M 1/3693; A61M 1/3696
See application file for complete search history.

(56) References Cited

U.S. PATENT DOCUMENTS 4,370,983 A * 2/1983 Lichtenstein ....... A61M 1/3621
　　　　　　　　　　　　　　　　　　　　　600/301
4,486,189 A * 12/1984 Troutner ................. A61M 1/30
　　　　　　　　　　　　　　　　　　　　　604/6.11
5,194,145 A 　 3/1993 Schoendorfer
(Continued)

FOREIGN PATENT DOCUMENTS

FR 　　 2867079 A1 * 9/2005 .............. A61M 1/30
JP 　 2014529409 A * 11/2014

OTHER PUBLICATIONS

Extended European Search Report for European Application No. 22189036.1 dated Nov. 18, 2022.

*Primary Examiner* — Rebecca E Eisenberg
*Assistant Examiner* — Ted Yang
(74) *Attorney, Agent, or Firm* — Cook Alex Ltd.

(57) ABSTRACT

Systems and methods for performing apheresis procedures, including photopheresis. The systems and methods utilize a disposable fluid circuit that can be converted from a double needle configuration to a single needle configuration and from a single needle configuration to a double needle configuration. A controller directs the action of system pumps to clear potentially stagnant blood residing in the fluid circuit, tracks system parameters and status before and after conversion, and verifies that the procedure may proceed in its new configuration.

19 Claims, 7 Drawing Sheets

(56)                References Cited

U.S. PATENT DOCUMENTS

|  |  |  |  |  |
|---|---|---|---|---|
| 5,403,291 | A * | 4/1995 | Abrahamson ....... | A61M 25/007 |
|  |  |  |  | 604/523 |
| 5,956,023 | A * | 9/1999 | Lyle ........................ | G16Z 99/00 |
|  |  |  |  | 604/4.01 |
| 6,027,657 | A | 2/2000 | Min et al. |  |
| 6,808,508 | B1 * | 10/2004 | Zafirelis .............. | A61M 1/3653 |
|  |  |  |  | 604/6.11 |
| 8,211,049 | B2 * | 7/2012 | Min ..................... | A61M 1/303 |
|  |  |  |  | 604/6.1 |
| 9,399,093 | B2 | 7/2016 | Min et al. |  |
| 9,744,288 | B2 | 8/2017 | Min et al. |  |
| 10,088,492 | B2 | 10/2018 | Wegener et al. |  |
| 10,172,995 | B2 | 1/2019 | Radwanski et al. |  |
| 10,213,544 | B2 | 2/2019 | Radwanski |  |
| 10,363,355 | B2 | 7/2019 | Prendergast et al. |  |
| 10,434,240 | B2 | 10/2019 | Abedin et al. |  |
| 10,518,020 | B2 | 12/2019 | Min et al. |  |
| 10,556,053 | B2 | 2/2020 | Abedin et al. |  |
| 10,751,433 | B2 | 8/2020 | Crawley et al. |  |
| 10,886,022 | B2 | 1/2021 | Ali et al. |  |
| 10,919,049 | B2 * | 2/2021 | Nguyen ................. | A61M 1/02 |
| 10,980,933 | B2 | 4/2021 | Prendergast et al. |  |
| 11,090,397 | B2 | 8/2021 | Min |  |
| 11,311,823 | B2 | 4/2022 | Kusters et al. |  |
| 11,318,239 | B2 | 5/2022 | Ali et al. |  |
| 2002/0151804 | A1 * | 10/2002 | O'Mahony ......... | A61M 1/3609 |
|  |  |  |  | 600/504 |
| 2005/0267400 | A1 * | 12/2005 | Haarala .............. | A61M 1/3661 |
|  |  |  |  | 604/523 |
| 2007/0100272 | A1 * | 5/2007 | Briggs ................. | B04B 5/0442 |
|  |  |  |  | 604/4.01 |
| 2009/0152200 | A1 * | 6/2009 | Lannoy ................... | A61M 1/34 |
|  |  |  |  | 210/201 |
| 2009/0166298 | A1 * | 7/2009 | Fender ................ | A61M 1/3696 |
|  |  |  |  | 210/101 |
| 2009/0198170 | A1 * | 8/2009 | Childers ................. | A61M 1/28 |
|  |  |  |  | 210/646 |
| 2010/0121246 | A1 * | 5/2010 | Peters ................. | A61M 1/3437 |
|  |  |  |  | 345/173 |
| 2010/0217174 | A1 * | 8/2010 | Min ........................ | A61M 1/30 |
|  |  |  |  | 604/6.01 |
| 2012/0297255 | A1 * | 11/2012 | Case ........................ | G08B 5/22 |
|  |  |  |  | 714/47.1 |
| 2013/0197419 | A1 | 8/2013 | Min et al. |  |
| 2014/0165733 | A1 * | 6/2014 | Jansson ................. | A61M 1/367 |
|  |  |  |  | 73/714 |
| 2014/0358061 | A1 * | 12/2014 | Cappella ............. | A61M 1/3639 |
|  |  |  |  | 210/103 |
| 2016/0055303 | A1 * | 2/2016 | Keller .................... | G16H 40/63 |
|  |  |  |  | 210/85 |
| 2016/0114095 | A1 | 4/2016 | Radwanski |  |
| 2017/0007758 | A1 * | 1/2017 | Kimura .................. | B04B 11/02 |
| 2017/0197023 | A1 | 7/2017 | Radwanski et al. |  |
| 2018/0036470 | A1 * | 2/2018 | Hasegawa ............. | A61M 1/301 |
| 2018/0078694 | A1 | 3/2018 | Abedin et al. |  |
| 2018/0256797 | A1 * | 9/2018 | Schenck ................. | A61M 1/72 |
| 2019/0099544 | A1 | 4/2019 | Abedin |  |
| 2019/0193091 | A1 * | 6/2019 | Nguyen ............. | A61M 1/3683 |
| 2019/0224494 | A1 | 7/2019 | Radwanski et al. |  |
| 2020/0107765 | A1 | 4/2020 | Abedin et al. |  |
| 2020/0222620 | A1 | 7/2020 | Ali et al. |  |
| 2020/0297914 | A1 | 9/2020 | Radwanski et al. |  |
| 2021/0043316 | A1 * | 2/2021 | Case ........................ | G08B 5/22 |
| 2021/0134431 | A1 * | 5/2021 | Garcia .................. | G16H 10/60 |
| 2021/0154390 | A1 | 5/2021 | Radwanski et al. |  |

* cited by examiner

Converting DN to SN

Converting SN to DN

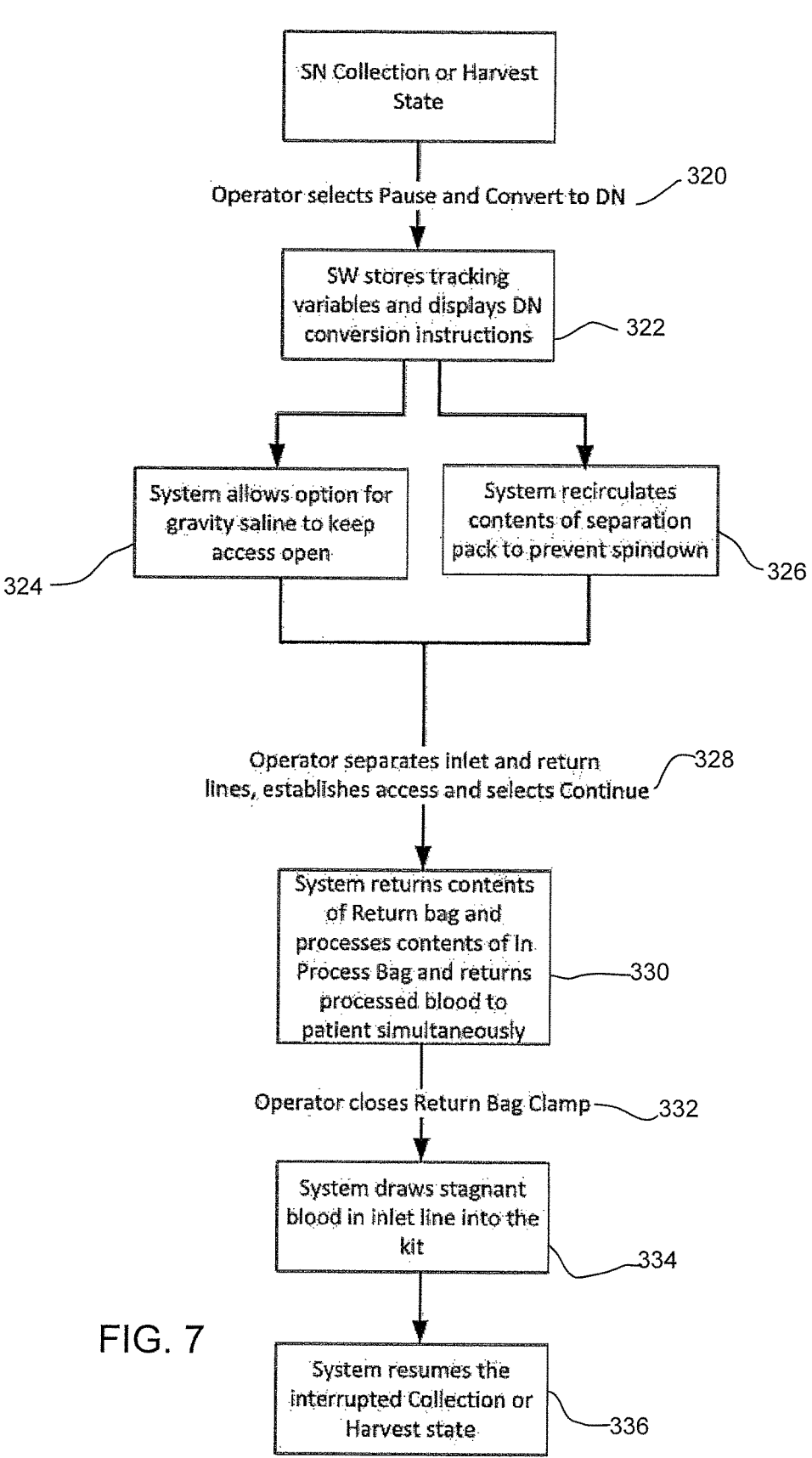

SN Collection or Harvest State

Operator selects Pause and Convert to DN — 320

SW stores tracking variables and displays DN conversion instructions — 322

System allows option for gravity saline to keep access open

324

System recirculates contents of separation pack to prevent spindown

326

Operator separates inlet and return lines, establishes access and selects Continue — 328

System returns contents of Return bag and processes contents of In Process Bag and returns processed blood to patient simultaneously — 330

Operator closes Return Bag Clamp — 332

System draws stagnant blood in inlet line into the kit — 334

FIG. 7

System resumes the interrupted Collection or Harvest state — 336

SYSTEMS AND METHODS FOR CONVERTING AN APHERESIS FLUID PROCESSING CIRCUIT TO SINGLE OR DOUBLE NEEDLE MODE

This application claims the benefit of and priority to U.S. Provisional Patent Application Ser. No. 63/230,473, filed on Aug. 6, 2021, the disclosure of which is incorporated herein by reference in its entirety.

FIELD OF THE DISCLOSURE

The present disclosure is directed to apheresis systems and methods for processing a biological fluid such as blood. More particularly, the present disclosure is directed to systems and methods for converting an apheresis fluid processing circuit to a single or double needle configuration. Even more particularly, the present disclosure is directed to systems and methods wherein during an apheresis procedure, a double needle apheresis fluid circuit can be converted to a single needle fluid circuit and a single needle fluid circuit can be converted to a double needle fluid circuit.

BACKQROUND

The various blood processing systems now make it possible to collect particular blood constituents, rather than whole blood, from donors or patients or other blood sources. Typically, in such systems, whole blood is drawn from a source, the particular blood component or constituent is removed and collected (and/or subjected to further treatment or processing) and the remaining blood constituents are returned to the source (donor or patient). This process of withdrawing whole blood from a donor or patient, separating components, and returning at least some of the components is commonly referred to as "apheresis." By thus removing only particular constituents, potentially less time is needed for the source's body to return to normal (in the case of a living source), and donations can be made at more frequent intervals than when whole blood is collected. This increases the overall supply of blood constituents, such as plasma and platelets, made available for health care.

Whole blood is typically separated into its constituents through centrifugation (although other separation principles, such as a spinning membrane as described in U.S. Pat. No. 5,194,145 may also be used.) This requires that the whole blood be passed through a centrifuge after it is withdrawn from, and before it is returned to, the source. To avoid contamination and possible infection of the source, the blood is typically contained within a sealed, sterile fluid flow system or disposable fluid circuit during the entire centrifugation process. The disposable fluid circuit may be equipped with one or more access devices or venipuncture needles for accessing the vascular system of the donor or patient. The venipuncture needles are in fluid communication with the tubing and containers of the disposable fluid circuit or "kit".

Typical blood processing systems thus include a permanent, reusable hardware (centrifuge and centrifuge drive system, pumps, valve actuators, programmable controller, and the like) that spins and pumps the blood, and a disposable fluid circuit that is mounted in cooperation on the reusable hardware. The centrifuge assembly engages and spins a separation chamber of the disposable fluid circuit during an apheresis procedure. The blood, however, makes actual contact only with the disposable fluid processing assembly, which assembly is used only once and then discarded.

As noted above, the disposable fluid circuit may be equipped with one or more needles for accessing the vascular system of the donor or patient. In a "single needle" configuration, blood is withdrawn from, and blood components are returned to the donor or patient through the same needle inserted into the vein of the patient or donor. The draw and return cycles are alternated with drawn blood being temporarily sequestered in an "in-process" container. During a return cycle, blood within the in-process container may be introduced into the separation chamber for processing. Similarly, the fluid circuit may include a "return container" which provides a temporary reservoir for separated fluid components during blood draw of a "single needle" procedure, with the contents of the return container subsequently being returned to the blood source (patient or donor) during a return phase.

In a "double needle" configuration, two needles are provided for drawing blood and returning blood components, respectively. The needles may be inserted into separate veins of the subject. Inasmuch as the withdrawal of whole blood and return of blood components are occurring concurrently when using a double needle fluid circuit, the in-process container and a return container may remain unused in a double needle configuration.

The disposable fluid circuit may be equipped and initially provided in a double needle configuration which can be converted to a single needle configuration, as necessary, to address certain events or disruptions that may occur during an apheresis procedure that may render one of the draw and return lines inoperative (e.g., due to a blockage). In this case, the incapacitated line may be directly connected to the viable line, with the procedure then continuing (in some capacity) with the fluid processing assembly in a "single needle" configuration instead of a "double needle" configuration. An example of a convertible fluid processing system and circuit is provided in U.S. Pat. No. 10,919,049, the contents of which are incorporated by reference herein in their entirety.

While the ability to convert a disposable fluid circuit from a double needle configuration to a single needle allows the apheresis procedure to continue notwithstanding a disruption due to blockage, further modifications to apheresis systems may be desired. For example, it may be desirable to convert a disposable fluid circuit in a single needle configuration to a double needle configuration. In addition, when converting the circuit or kit from a double needle configuration to a single needle configuration, parts of the circuit may include stagnant, unanticoagulated blood that may clot and affect blood flow within the fluid circuit. Accordingly, it would be desirable for the controller-based system to flush or otherwise remove any such stagnant and unanticoagulated blood. Inasmuch as the conversion of the apheresis procedure from a single needle to double needle procedure or from a double needle to a single needle procedure will often require a pause in the procedure followed by a resumption of the procedure, it would be desirable to have a system that can verify that the conversion has been correctly completed and that the procedure may resume in its new configuration. Finally, it would be desirable to have a system that tracks multiple parameters of the apheresis procedure and initializes the appropriate variable in the converted single needle or double needle procedure.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a system for performing an apheresis procedure is provided. The system includes a reusable, fluid processing device, wherein the device includes valves for opening and closing flow paths of a fluid circuit, one or more pumps for moving blood through the flow paths of a fluid circuit and a controller. The system also includes a disposable fluid circuit mountable onto the device, the circuit including a separation chamber, a draw line including a fluid source access device (needle) wherein the draw line is in flow communication with the chamber, and a return line including a fluid source access device (needle) wherein the draw line is in flow communication with the separation chamber. A controller is included and is configured to (i) provide instructions for converting the disposable fluid circuit from a double needle configuration to a single needle configuration, and/or (ii) provide instructions for converting said disposable fluid circuit from a single needle configuration to a double needle configuration, and (iii) perform one or more checks to verify that the apheresis procedure may continue in the converted configuration.

In another aspect, the present subject matter is directed to a method for performing an apheresis procedure. The method includes establishing fluid communication with the vascular system of a donor or patient by inserting one or two needles of a disposable fluid circuit into said one or more veins of said donor or patient; initiating an apheresis procedure by withdrawing blood through a needle of the disposable fluid circuit; pausing the apheresis procedure; reconfiguring the fluid circuit by changing the number of needles in fluid communication with the vascular system of the donor or patient; and resuming the apheresis procedure with said disposable fluid circuit in said reconfigured state.

The systems and methods described herein find application in apheresis procedures generally as well as in apheresis procedures which include or are combined with further treatment of a collected blood component such as the photoactivation treatment of mononuclear cells, commonly referred to as "photopheresis."

BRIEF DESCRIPTION OF THE DRAWINGS

FIG. 7 is a flow chart showing the automated and operator-initiated steps during a conversion of a fluid circuit from a single needle configuration to a double needle configuration.

DETAILED DESCRIPTION OF THE EMBODIMENTS

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting and should be understood to encompass variations or embodiments that would occur to persons of ordinary skill.

Figure 1:
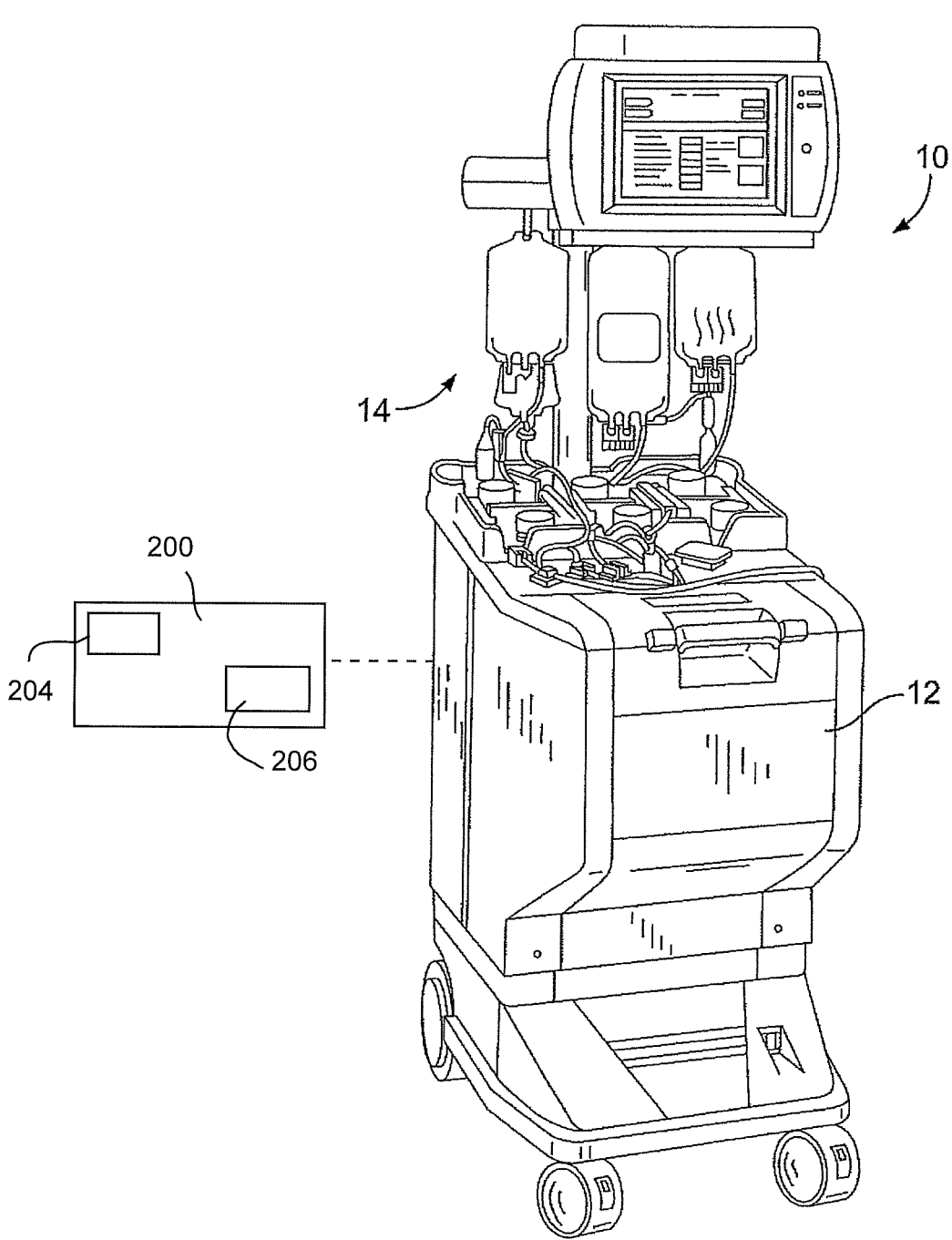
FIG. 1 is a perspective view of an apheresis system in accordance with the present disclosure.
Figure 2:
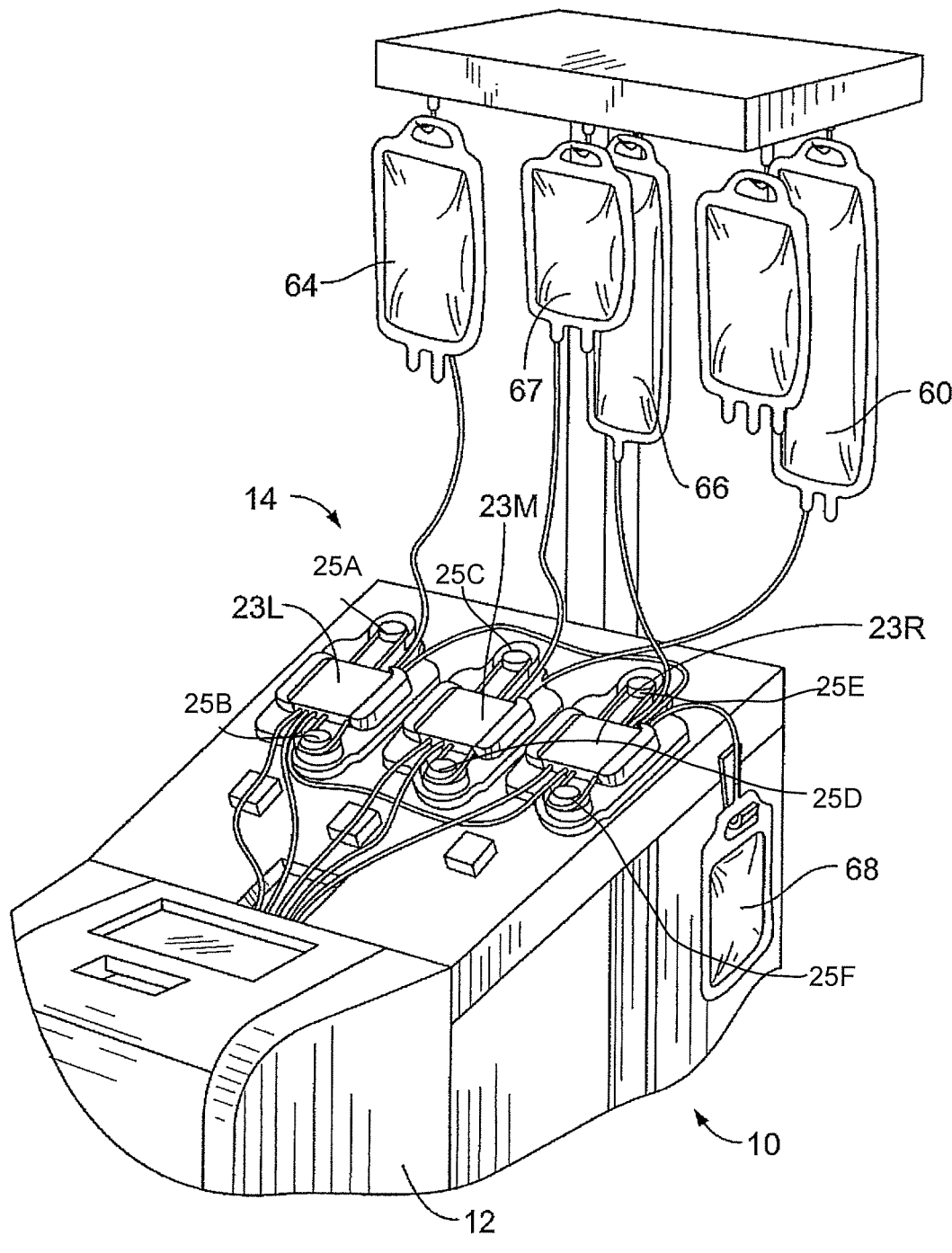
FIG. 2 is an enlarged perspective view of the front panel the apheresis system of FIG. 1 with a disposable fluid circuit mounted thereon.

FIGS. 1 and 2 show a representative apheresis system 10 useful in the separation of whole blood and collection of blood components. The system 10 includes a reusable hardware component 12 and a disposable fluid circuit or kit 14 that is mounted thereon. In one embodiment, the separation principle used by the separator 12 is based on centrifugation, but an automated separator based on a different separation principle may also be used.

Figure 3:
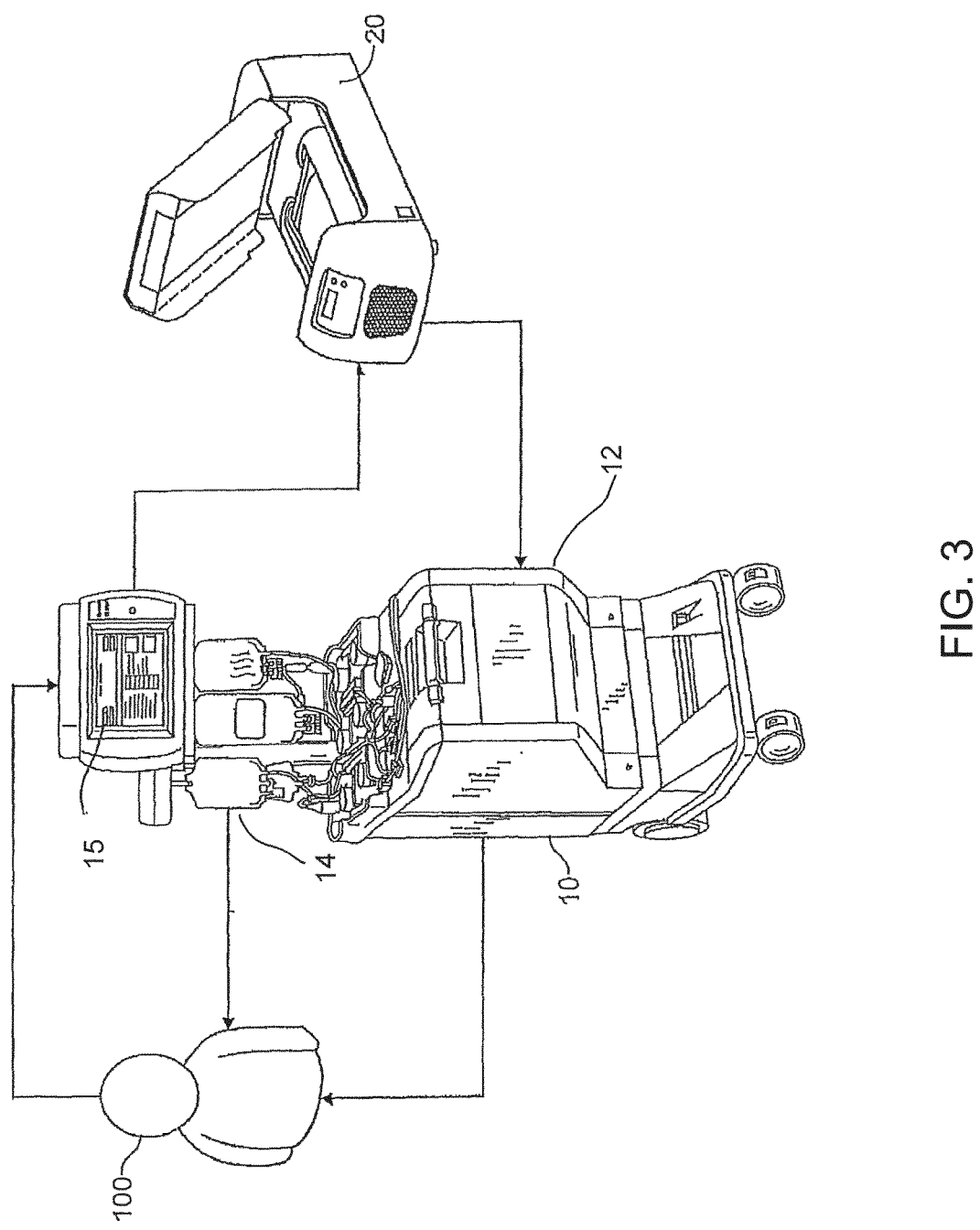
FIG. 3 is a schematic view of the apheresis system of FIGS. 1 and 2 in combination with an irradiation device and a patient embodying an apheresis/photopheresis system in accordance with the present disclosure.

When used to perform photopheresis, an irradiation component 20 housed separately from hardware component 12 is used in conjunction with the separation system 10, as shown schematically in FIG. 3 and described in US 2013/0197419, which is incorporated herein by reference. Although separately housed and independent devices, it is preferable that separation device/component 12 and irradiation device 20 be located adjacent to each other. However, it will be appreciated that the methods described herein may also be used with devices having integrated separation and irradiation components.

In accordance with the systems and methods described herein, a patient (or donor) is connected to disposable fluid circuit 14. As noted above, the fluid circuit 14 provides a sterile closed pathway between the separation component 12 and the irradiation component 20.

In accordance with the present disclosure, whole blood is withdrawn from the patient (or donor) and introduced into the separation component 12, where the whole blood is separated to provide a target cell population, which in the context of photopheresis may be mononuclear cells. Other components separated from the whole blood, such as red blood cells and platelets may be returned to the patient or collected in pre-attached containers of the blood processing set. The separated target cell population, e.g., mononuclear cells, may be prepared for and subjected to a photoactivation treatment.

Apparatus useful in the collection of mononuclear cells, and providing the separation component 12 of FIG. 1, include the Amicus® Separator made and sold by Fenwal, Inc., of Lake Zurich, Illinois, which is an affiliate of Fresenius Kabi AG of Bad Homburg, Germany. Mononuclear cell collections using a device such as the Amicus® are described in greater detail in U.S. Pat. No. 6,027,657, the contents of which is incorporated by reference herein in its entirety. The fluid circuit (FIG. 4) includes a blood processing container 16 defining a separation chamber suitable for separating and harvesting mononuclear cells (MNC) from whole blood.

As shown in FIG. 2, disposable processing set or fluid circuit 14 (which includes container 16) is mounted on the front panel of the separation component 12. The fluid circuit 14 includes a plurality of processing fluid flow cassettes 23L, 23M and 23R with tubing loops for association with peristaltic pumps 25A-25F on the separation component 12. Fluid circuit 14 also includes a network of tubing and pre-connected containers for establishing flow communication with the patient and for processing and collecting fluids and blood and blood components, as shown in greater detail in FIG. 4 and described below.

Figure 4:
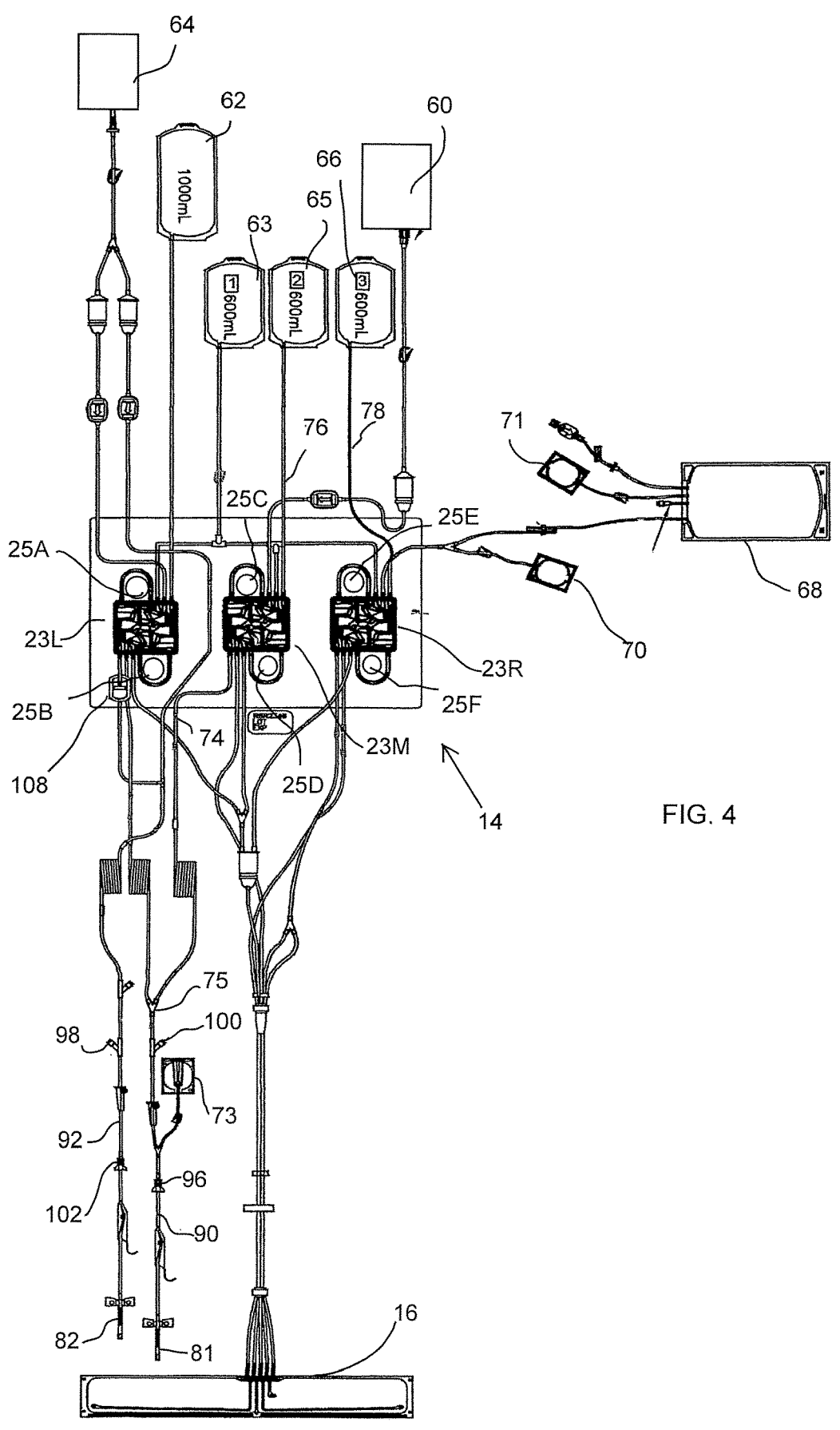
FIG. 4 is a schematic view of disposable fluid circuit for use with the apheresis/photopheresis system of FIG. 3.

As further seen in FIG. 4, the disposable processing set 14 may include a container 60 for supplying anticoagulant, waste container 62 for collecting waste from one or more steps in the process for treating mononuclear cells, container 63 for temporarily holding components to be returned to the donor or patient, container 64 for holding a crystalloid solution, such as saline, or other wash or resuspension medium, in-process container 65 for temporarily holding blood components to be processed, container 66 for collecting plasma, container 68 for collecting the desired blood component which, in a photopheresis system and method may be mononuclear cells and, optionally, a container (not shown) for holding photoactivation agent. In a photopheresis procedure, container 68 may also serve as the illumination container and is preferably pre-attached to disposable set 14. Alternatively, container 68 may be attached to set 14 by known sterile connection techniques, such as sterile docking or the like. Disposable fluid circuit 14 may further include sample pouches 70 and 71 for collecting samples of the collected component (such as mononuclear cells) before and after photoactivation. Fluid circuit 14 may also include sampling pouch 73 for the pre-donation sampling of whole blood.

With further reference to FIG. 4, fluid circuit includes draw line 72, an anticoagulant (AC) line 74 for delivering AC from container 60. Anticoagulant line 74 joins draw line 90 at branch member 75. Fluid circuit 14 further includes a red blood cell (RBC) line 76 for conveying red blood cells from the separation chamber of container 16 to container 65, a platelet-poor plasma (PPP) line 78 for conveying PPP from separation chamber 16 to container 66 and line 80 for conveying mononuclear cells to and from separation chamber 16 and collection/illumination container 68.

The blood processing set also includes one or more venipuncture needle(s) for accessing the vascular system of the patient. As shown in FIG. 4, fluid circuit 14 includes inlet needle 81 and return needle 82. In accordance with the present disclosure, disposable fluid circuit 14 may initially be provided in a double needle configuration, as shown. In the event that access to draw line 90 has become impaired or rendered inoperative, draw line 90 may be directly connected to the return line 92 for continued processing. In that regard, draw line 90 and return line 92 are provided with mating connectors 96 and 98 that are directly connected to convert the fluid circuit 14 from a "double needle" configuration to a "single needle" configuration, as shown in greater detail in FIG. 5, in which the return line 92 is responsible for both fluid draw and return. In one embodiment, connector 96 of the draw line 90 is configured as a male luer, while the connector 98 on the return line 92 is configured as a female luer, but the exact configuration of the mating connectors 96 and 98 may vary without departing from the scope of the present disclosure.

Figure 6:
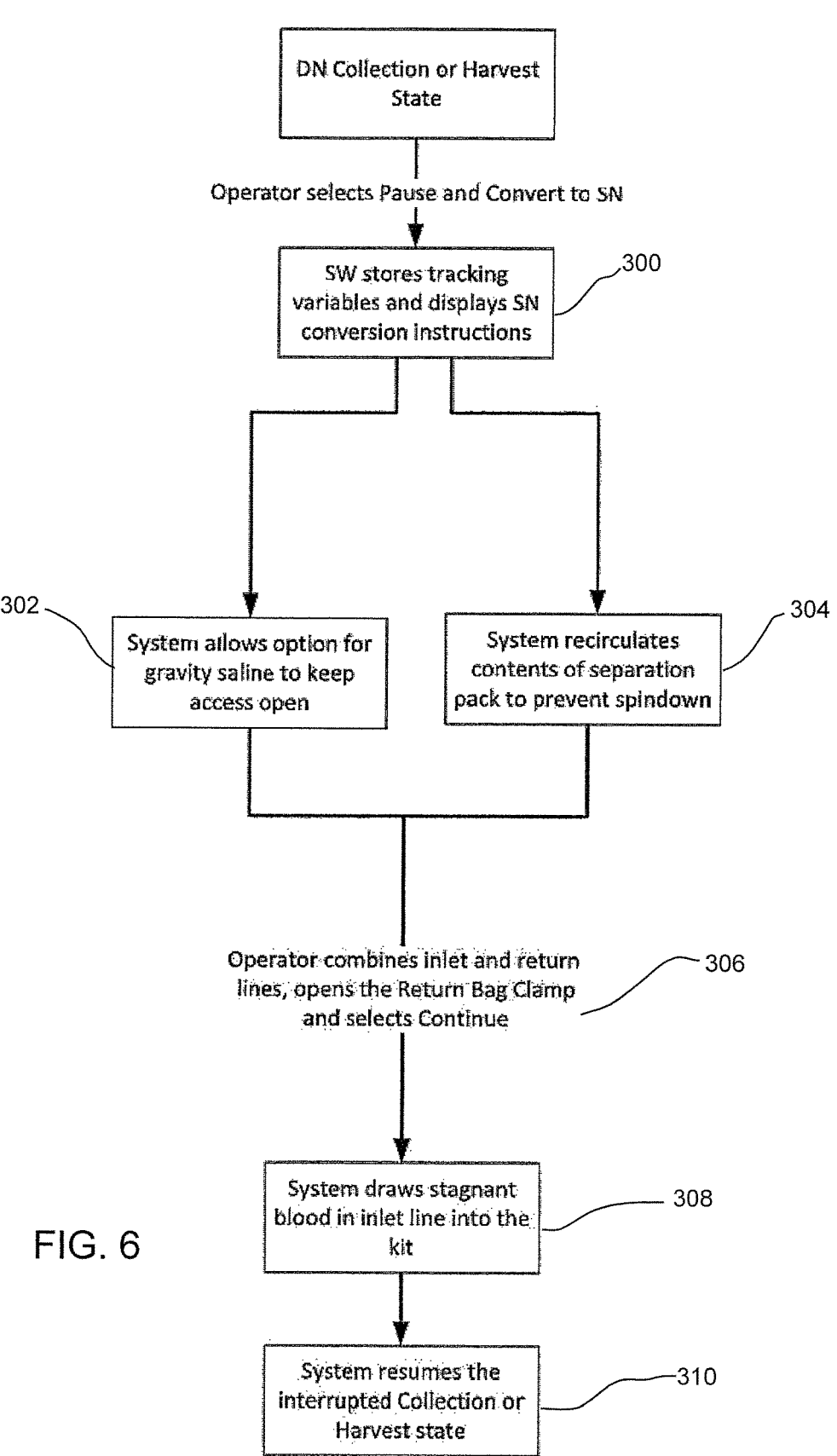
FIG. 6 is a flow-chart showing the automated and operator-initiated steps during a conversion of a fluid circuit from a double needle configuration to a single needle configuration.

When converting fluid circuit 14 from a double needle configuration to single needle configuration such that return line 92 is responsible for both fluid draw and return (i.e., where the luer connector on the draw line 90 is connected to the luer on the return line 92), care must be taken to ensure that unanticoagulated and potentially stagnant blood in the impaired draw line 90 does not clot and block the flow paths of the fluid circuit 14. Accordingly, soon if not immediately after conversion from a double needle configuration conversion to a single needle configuration (or from a single needle configuration to a double needle configuration) any stagnant, unanticoagulated in draw line 90 may be drawn (pumped by one or more pumps, such as pumps 25A and 25C, under the direction of controller 200) into the disposable fluid circuit, and directed through return line filter 108 to remove any potential clots that may have formed so as to avoid blockage in the centrifuge lines and returned to patient. As noted above, this "one time" post-conversion clearing of stagnant, unanticoagulated blood is preferably performed immediately after conversion from one configuration to another configuration (see also, FIGS. 6 and 7).

Figure 5:
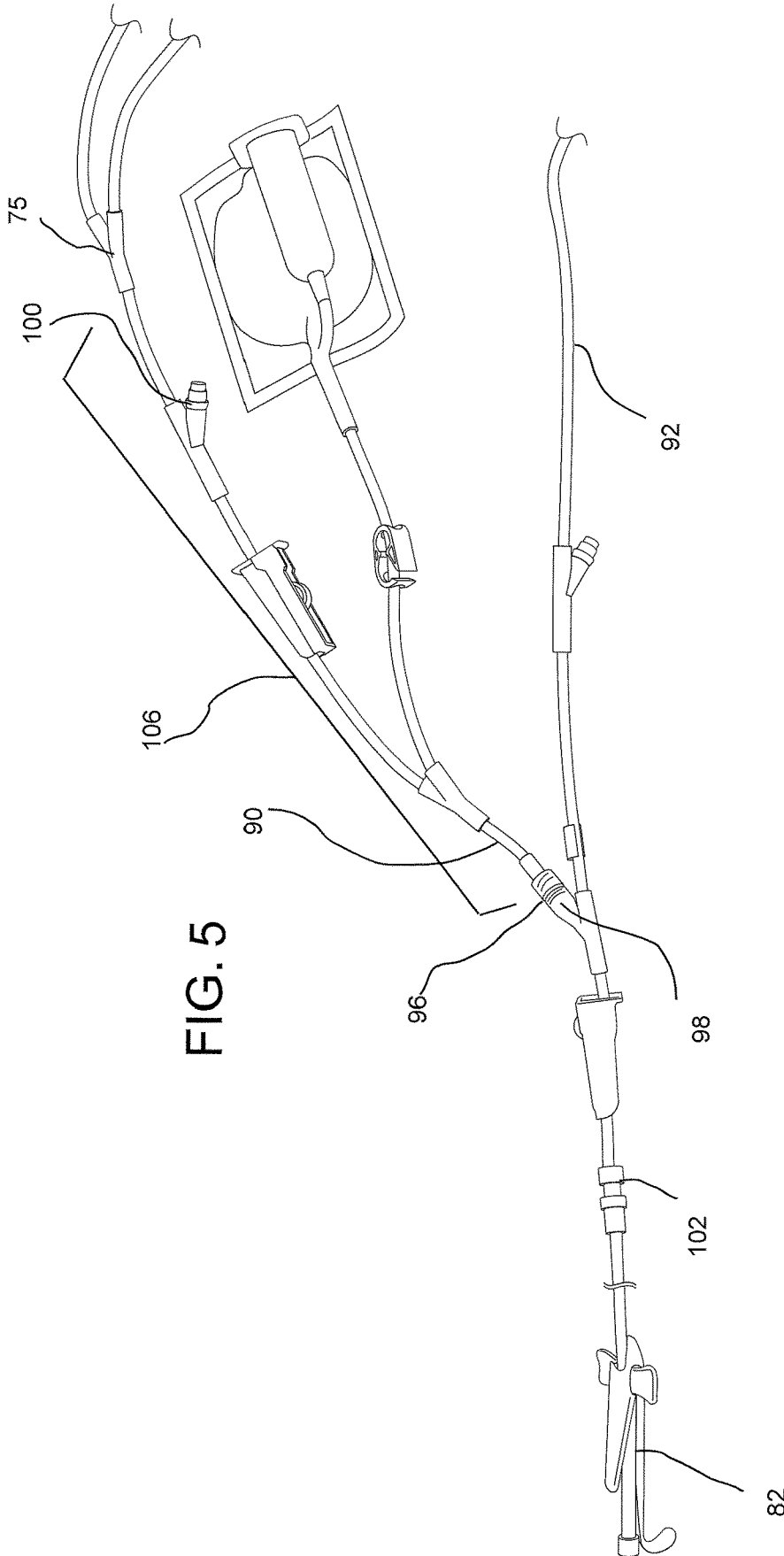
FIG. 5 is a partial view of the disposable fluid circuit of FIG. 4 wherein the circuit has been reconfigured from a double needle configuration to a single needle configuration.

In addition to the foregoing, where a double needle configuration has been converted to a single needle configuration, additional and repeating "clearing" of stagnant, unanticoagulated blood may be desired. For example, as seen in FIG. 5, blood residing in the portion 106 of draw line 90 (now connected to return line 92) below branch member 75 is unlikely to be anticoagulated and is stagnant during the return cycle, and may become coagulated if the return cycle is long in duration. In accordance with the method and system described herein, stagnant blood residing in portion 106 of the fluid circuit may be cleared prior to each return cycle, as described below.

In one embodiment (and with reference to FIGS. 4 and 5), blood components residing in return container 63 may be pumped by pump 25A, under the direction of controller 200, through the draw line 90 and displace any potentially stagnant blood in circuit portion 106. Alternatively, saline or other crystalloid solution may be pumped by one or more pumps, under the direction of controller 200, through draw line 90 to likewise displace any potentially stagnant blood residing in circuit portion 106, although pumping fluid from return container 63 may be preferred inasmuch as this method uses the patient's own blood instead of saline of which an excess amount can be harmful to the patient. While pumping either return fluid or saline allows for better control over volume displacement, the stagnant blood in fluid circuit portion 106 may also be cleared by gravity draining return fluid or saline from containers 63 or 64, respectively. The unanticoagulated blood may be displaced to a point where connectors 96 and 98 are joined (see FIG. 5) to ensure that it is returned during the next return cycle. (FIG. 4)

In an alternative embodiment, where return line 92 has been rendered inoperative, it may be directly connected to the draw line 90 for continued processing in a manner that is similar to the double needle to single needle conversion described above. As described above, the draw line 90 and return line 92 are provided with mating connectors 100 and 102 that are directly connected to convert the fluid circuit 14 from a "double needle" configuration to a "single needle" configuration in which now the draw line 90 is responsible for both fluid draw and return. Connector 100 of the draw line 90 may be configured as a female luer, while the connector 102 on the return line 92 is configured as a male luer, but the exact configuration of the mating connectors 100 and 102 may vary without departing from the scope of the present disclosure.

In a further alternative embodiment, fluid circuit 14 may be converted from a single needle configuration to a double needle configuration. In this regard, a previously established luer connection whereby a double needle configuration had been converted to a single needle configuration may be undone and the draw and return lines 90,92 separated. Male luer 96 on draw line 90 or male luer 102 on return line 92 may be connected to a new venipuncture needle 81 or 82 assembly to convert the fluid circuit (back) to a double needle configuration.

Fluid flow through fluid circuit 14 is preferably driven, controlled, and adjusted by a microprocessor-based controller 200 in cooperation with the valves, pumps, weight scales and sensors of separation component 12 and fluid circuit 14, the details of which are described in the previously mentioned U.S. Pat. No. 6,027,657. As discussed above, controller 200 may also initiate pump rotation to pump return fluid or saline to clear stagnant blood residing in the fluid circuit 14 and fluid circuit portion 106 specifically.

Controller 200 (schematically shown in FIG. 1) may include a microprocessor 204 (which may include multiple physical and/or virtual processors). According to other embodiments, the controller 200 may include one or more electrical circuits designed to carry out the actions described herein. In an embodiment, controller 200 may include a microprocessor and other circuits or circuitry. In addition, the controller 200 may include one or more memories 206. The instructions by which the microprocessor is programmed may be stored on the memory 206 associated with the microprocessor 204, which memory/memories 206 may include one or more tangible non-transitory computer readable memories, having computer executable instructions stored thereon, which when executed by the microprocessor 204, may cause the microprocessors 204 and associated software to carry out one or more actions as described herein.

The processing following conversion from a "double needle" configuration to a "single needle" configuration or conversion from a "single needle" to a "double needle" configuration may vary depending on a number of factors, including the current procedure state or phase at the time of conversion. The controller of the fluid processing system 10 may monitor or track at least one or more of the amount of whole blood processed, the amount of whole blood withdrawn, the amount of whole blood returned, the current procedure state (such as, but not limited to, an initial processing state, a plasma collection state, a MNC collection state, a red blood cell collection state), the current extracorporeal volume, current red blood cell volume, the current fluid balance and use that information to determine how to proceed once processing is unpaused/continued after conversion from one configuration to another configuration. The controller may also initialize the appropriate variables unique to either a single needle procedure or a double needle procedure in the new single needle or double needle configuration. Depending on the circumstances, the controller may determine that it is appropriate to continue the procedure state or phase that was being executed at the time of termination. If the controller instead determines that it would be inappropriate to continue with the procedure state or phase that was being executed at the time of termination, then it may instead initiate a different procedure state or phase, which may be the phase or procedure state immediately following the phase or procedure state that was being executed at the time of termination, a variation of such succeeding phase or procedure state, or some other phase or procedure state Conversion from a double needle configuration to a single needle configuration may be initiated at any time during the collection or harvesting of blood components. The operator may begin the conversion process by selecting "Pause and Convert to SN" on the graphical user interface/touch screen 15 of hardware unit 12 (FIG. 1). Controller 200 stores the tracking variables and displays "SN" conversion instructions on the user interface 15 or other computer screen, as shown in step 300 of FIG. 6. The system allows for gravity delivery of saline to keep access to the patient open and facilitate the return of blood components and/or recirculate contents in separation chamber 16 to prevent spindown as shown in steps 302 and 304. "Spindown" refers to a condition of the separator whereby flow through the separator (e.g., centrifuge) during the pause in the procedure to allow for conversion results is diminished flow and consequently, an automatic "spinning down" of the centrifuge so as to prevent heating of the blood. To prevent the automatic spindown, a small volume of blood is recirculated slowly through the centrifuge. The operator then performs the manual conversion by combining the draw and return lines, opens the Return container clamp and selects "Continue" on the screen (step 306). The system then draws stagnant blood into the kit (step 308), as described above, and resumes collection/harvesting in its new configuration.

Conversion from a single needle configuration to a double needle configuration is shown in FIG. 7. As in the double needle to single needle conversion, the operator selects Pause and Convert to DN on the graphical user interface or computer screen (step 320). Controller 200 stores the tracking variables and displays DN conversion instructions on the user interface 15 or other computer screen, as shown in step 322. The system allows for gravity delivery of saline to keep access open and/or recirculates contents in separation chamber 16 to prevent spindown as shown in steps 324 and 326. The operator then performs the manual conversion of the single need kit to a double needle kit, as previously described (step 328). Under the direction of the controller, the system then returns the previously collected (while in the single needle configuration) contents of the return container 63 and processes the contents of in-process container 65. Processed blood components are then returned to the patient simultaneously with the return fluid (step 330). The operator then closes the clamp to return container 63 (step 332). Under the direction of the controller, the system then draws stagnant blood in the inlet line into the kit (step 334) and the system resumes the collection and harvesting of components.

OTHER EXAMPLES

Aspects of the present subject matter described above may be beneficial alone or in combination with one or more other Aspects, as described below.

Aspect 1. A system for performing an apheresis procedure including a reusable, fluid processing device, the device comprising valves for opening and closing flow paths of a fluid circuit, one or more pumps for moving blood through flow paths of a fluid circuit and a controller. The system includes a disposable fluid circuit mountable onto the fluid processing device, the circuit comprising a separation chamber, a draw line including a fluid source access device wherein the draw line is in flow communication with the chamber, and a return line including a fluid source access device wherein the return line is in flow communication with the chamber. The controller is configured to (i) provide instructions for converting the disposable fluid circuit from a double needle configuration to a single needle configuration and/or (ii) provide instructions for converting the disposable fluid circuit from a single needle configuration to a double needle configuration and to (iii) perform one or more checks to verify that the apheresis procedure may continue in the converted configuration.

Aspect 2. The system of Aspect 1 wherein the controller is further configured to monitor one or more of the following procedure parameters: (a) volume of whole blood processed (b) volume of whole blood drawn from a blood source (c) volume of whole blood returned (d) current procedure state (e) current extracorporeal volume (f) current red blood cell volume removed from source (g) current fluid balance of source.

Aspect 3. The system of any one of Aspects 1 and 2 wherein the draw line includes a connection site for the return line and the return line includes a connection site for the draw line.

Aspect 4. The system of any one of Aspects 1 through 3 wherein the controller is configured to pause the apheresis procedure during conversion from one configuration to another configuration and resume the apheresis procedure once the conversion has been completed.

Aspect 5. The system of any one of Aspects 1 through 4 wherein the disposable fluid circuit further comprises an in-process container for holding blood or a blood component to be processed and a return container for holding a blood component to be returned to a blood source.

Aspect 6. The system of Aspect 5 wherein the controller is further configured to initiate processing of the blood in the in-process container and initiate return of the blood component in the return container to the source.

Aspect 7. The system of Aspect 6 wherein the controller is configured to initiate processing of the blood in the in-process container and initiate return of the blood component in the return container to the source after converting the disposable fluid circuit from a single needle configuration to a double needle configuration.

Aspect 8. The system of any one of Aspects 1 through 7 further comprising a filter on the return line.

Aspect 9. The system of Aspect 8 wherein said controller is further configured to initiate flow of unanticoagulated blood through the filter.

Aspect 10. The system of any one of Aspects 1 through 9 wherein the draw line includes an access port for receiving said return line.

Aspect 11. The system of any one of Aspects 1 through 10 wherein the return line includes an access port for receiving said draw line.

Aspect 12. A method for performing an apheresis procedure comprising: establishing fluid communication with the vascular system of a donor or patient by inserting one or two needles of a disposable fluid circuit into said one or more veins of the donor or patient; initiating an apheresis procedure by withdrawing blood through a needle of the disposable fluid circuit; pausing the apheresis procedure; reconfiguring the fluid circuit by changing the number of needles in fluid communication with the vascular system of the donor or patient; and resuming the apheresis procedure with the disposable fluid circuit in said reconfigured state.

Aspect 13. The method of Aspect 12 comprising establishing fluid communication with the donor or patient by inserting a first needle of a draw line into one vein of the donor or patient and inserting a second needle of a return line into another vein of the donor or patient.

Aspect 14. The method of Aspect 13 comprising reconfiguring the fluid circuit by detaching one of the draw and return lines from said circuit and establishing fluid communication between the detached line and said disposable fluid circuit at a different location of said circuit.

Aspect 15. The method of Aspect 14 further comprising establishing fluid communication between the detached line and the disposable fluid circuit at a location on the circuit that is downstream of the first or second needles.

Aspect 16. The method of any one of Aspects 14 through 15 comprising clearing unanticoagulated blood residing within the disposable fluid circuit.

Aspect 17. The method of Aspect 16 wherein said unanticoagulated blood is passed through a filter.

Aspect 18. The method of Aspect 12 comprising establishing fluid communication with the vascular system of a donor or patient by inserting one needle of a draw or return line of said disposable fluid circuit into a vein of said donor or patient and inserting a connector on said other of said draw or return line into an access port on a line that is in flow communication with the one needle.

Aspect 19. The method of Aspect 18 comprising reconfiguring the fluid circuit by removing the connector from the access port and establishing flow communication with one of the draw and return lines.

Aspect 20. The method of Aspect 19 comprising returning blood from a return container of the disposable fluid circuit to the donor or patient prior to resuming the apheresis procedure.

Aspect 21. The method of Aspect 20 further comprising returning blood from an in-process container to the donor or patient prior to resuming the apheresis procedure.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A system for performing an apheresis procedure comprising:
   a) a reusable, fluid processing device, said device comprising valves for opening and closing flow paths of a disposable fluid circuit, one or more pumps for moving blood through flow paths of the disposable fluid circuit, a controller, and a user interface;
   b) the disposable fluid circuit, wherein the disposable fluid circuit is mountable onto said device, said circuit comprising a separation chamber, a draw line including a fluid source access device wherein said draw line is in flow communication with said chamber, and a return line including a fluid source access device wherein said return line is in flow communication with said chamber, wherein the return line comprises a filter; and
   c) wherein said controller is configured to (i) provide and display instructions on the user interface for converting said disposable fluid circuit from a double needle configuration to a single needle configuration and (ii) provide and display instructions on the user interface for converting said disposable fluid circuit from a single needle configuration to a double needle configuration, (iii) recirculate blood through the separation chamber during conversion of the disposable fluid circuit from the double needle configuration to the single needle configuration and from the single needle configuration to the double needle configuration, (iv) perform one or more checks to verify that the apheresis procedure may continue in a converted configuration, and (v) clear stagnant unanticoagulated blood from the return line or the draw line after placing the disposable fluid circuit in the converted configuration and initiate flow of the unanticoagulated blood through the filter in the return line.

2. The system of claim 1 wherein said controller is further configured to monitor one or more of the following procedure parameters: (a) volume of whole blood processed, (b) volume of whole blood drawn from a blood source, (c) volume of whole blood returned, (d) current procedure state, (e) current extracorporeal volume, (f) current red blood cell volume removed from said blood source, and (g) current fluid balance of said blood source.

3. The system of claim 1, wherein said draw line includes a draw line mating connector for said return line and said return line includes a return line mating connector for said draw line.

4. The system of claim 1, wherein said controller is configured to pause said apheresis procedure during conversion from one configuration to another configuration and resume said apheresis procedure once said conversion has been completed.

5. The system of claim 1 wherein said disposable fluid circuit further comprises an in-process container for holding blood or a blood component to be processed and a return container for holding a blood component to be returned to a blood source.

6. The system of claim 5 wherein said controller is further configured to initiate processing of said blood in said in-process container and initiate return of said blood component in said return container to said source.

7. The system of claim 6 wherein said controller is configured to initiate processing of said blood in said in-process container and initiate return of said blood component in said return container to said source after converting said disposable fluid circuit from a single needle configuration to a double needle configuration.

8. The system of claim 1, wherein said draw line includes an access port for receiving said return line.

9. The system of claim 1, wherein said return line includes an access port for receiving said draw line.

10. A method for performing an apheresis procedure comprising:

a) establishing fluid communication with a vascular system of a donor or patient by inserting one or two needles of a disposable fluid circuit into one or more veins of said donor or patient;

b) initiating an apheresis procedure by withdrawing blood through a needle of said disposable fluid circuit;

c) pausing said apheresis procedure;

d) reconfiguring said fluid circuit to a reconfigured state by changing the number of needles in fluid communication with the vascular system of said donor or patient; and e) resuming said apheresis procedure with said disposable fluid circuit in said reconfigured state.

11. The method of claim 10 comprising establishing fluid communication with said donor or patient by inserting a first needle of a draw line into one vein of the donor or patient and inserting a second needle of a return line into another vein of the donor or patient.

12. The method of claim 11 comprising reconfiguring said fluid circuit by detaching one of said draw and return lines from said circuit and establishing fluid communication between said detached line and said disposable fluid circuit at a different location of said circuit.

13. The method of claim 12 further comprising establishing fluid communication between said detached line and said disposable fluid circuit at a location on said circuit that is downstream of said first or second needles.

14. The method of claim 12 comprising clearing unanticoagulated blood residing within said disposable fluid circuit.

15. The method of claim 14 wherein said unanticoagulated blood is passed through a filter.

16. The method of claim 10 comprising establishing fluid communication with the vascular system of a donor or patient by inserting one needle of a draw or return line of said disposable fluid circuit into a vein of said donor or patient and inserting a connector on said other of said draw or return line into an access port on a line that is in flow communication with said one needle.

17. The method of claim 16 comprising reconfiguring said fluid circuit by removing said connector from said access port and establishing flow communication with one of a draw and return lines.

18. The method of claim 17 comprising returning blood from a return container of said disposable fluid circuit to said donor or patient prior to resuming said apheresis procedure.

19. The method of claim 18 further comprising returning blood from an in-process container to said donor or patient prior to resuming said apheresis procedure.

* * * * *